US006994550B2

(12) United States Patent
Knapp et al.

(10) Patent No.: US 6,994,550 B2
(45) Date of Patent: Feb. 7, 2006

(54) VAPOR DEPOSITED TITANIUM AND TITANIUM-NITRIDE LAYERS FOR DENTAL DEVICES

(75) Inventors: Kenneth E. Knapp, Livermore, CA (US); Michael L. Hedrick, Livermore, CA (US)

(73) Assignee: Nano-Write Corporation, Livermore, CA (US)

( * ) Notice: Subject to any disclaimer, the term of this patent is extended or adjusted under 35 U.S.C. 154(b) by 106 days.

(21) Appl. No.: 10/622,626

(22) Filed: Jul. 17, 2003

(65) Prior Publication Data

US 2004/0121291 A1   Jun. 24, 2004

Related U.S. Application Data

(60) Provisional application No. 60/436,177, filed on Dec. 23, 2002.

(51) Int. Cl.
*A61C 13/08* (2006.01)
*A61C 5/08* (2006.01)
*A61C 5/10* (2006.01)

(52) U.S. Cl. ............... 433/207; 433/218; 433/223; 427/2.26

(58) Field of Classification Search .......... 433/207, 433/218, 223; 106/35; 427/2.1, 2.11, 2.24, 427/2.26, 2.29
See application file for complete search history.

(56) References Cited

U.S. PATENT DOCUMENTS

| 4,451,236 | A | * | 5/1984 | Tarasov et al. ............. 433/207 |
| 5,226,913 | A | * | 7/1993 | Pinchuk .................... 140/71 R |
| 5,314,334 | A | * | 5/1994 | Panzera et al. ............. 433/206 |
| 5,346,396 | A | * | 9/1994 | Hakamatsuka ............. 433/208 |
| 5,843,117 | A | * | 12/1998 | Alt et al. .................. 623/1.15 |
| 2002/0007209 | A1 | * | 1/2002 | Scheerder et al. ......... 623/1.15 |
| 2004/0063059 | A1 | * | 4/2004 | Meckel ........................ 433/8 |

* cited by examiner

*Primary Examiner*—Cary E. O'Connor
(74) *Attorney, Agent, or Firm*—Mark Lauer; Silicon Edge Law Group LLP

(57) ABSTRACT

A coating for a biomedical device is disclosed, including a metal layer and/or a ceramic layer, such as a layer of titanium (Ti) and a layer of titanium-nitride (TiN). The coating can form a coping for a crown for a tooth, the crown including a porcelain layer bonded to the titanium-nitride (TiN) layer. Methods for making and using a biomedical device are also disclosed, including vapor deposition of metal and/or ceramic layers, such as titanium (Ti) and titanium-nitride (TiN) layers. In one embodiment, the method includes forming a titanium (Ti) vapor that solidifies to form a titanium (Ti) layer; forming a titanium-nitride (TiN) vapor that coats the titanium (Ti) layer with a titanium-nitride (TiN) layer; and forming a porcelain layer on the titanium-nitride (TiN) layer. The porcelain can be sintered to form a dental crown or other device.

23 Claims, 5 Drawing Sheets

VAPOR DEPOSITED TITANIUM AND TITANIUM-NITRIDE LAYERS FOR DENTAL DEVICES

CROSS-REFERENCE TO RELATED APPLICATIONS

The present application claims the benefit under 35 U.S.C. §119 of Provisional Application Ser. No. 60/436,177, filed Dec. 23, 2002, which is incorporated by reference herein.

BACKGROUND

The present application relates to biomedical devices, such as dental crowns, bridges and implants, and other devices that can be employed within people or animals.

The manufacture of dental devices such as crowns has traditionally been a labor-intensive process. After a dentist has ground away parts of a patient's tooth to leave a protruding tooth stub, an impression of the stub is taken, typically along with an impression of the surrounding and opposing teeth. The impression is typically sent to a dental laboratory, which makes a mold from the impression of the stub, the mold commonly made of gypsum and called a die stone. For crowns that are made completely of metal such as gold, silver, palladium or stainless steel, a wax replica of the tooth is then hand crafted on the die stone, and the wax tooth replica is then invested in a material that solidifies. As that material is heated the wax is melted or burned out. The molten metal is then poured into a void created by the lost wax, and cools to become the crown.

Conventional fabrication of porcelain crowns is complicated by attempting to match the crown to the color of the surrounding teeth. In this case, the crown is usually formed atop a metal coping that may impart a color that is apparent through translucent porcelain. For instance, a titanium (Ti) coping readily oxidizes to have a titanium oxide (TiO or $TiO_2$) film, which is black and can affect the color of the porcelain crown.

Such a metal coping is usually made by the lost wax technique to fit atop the tooth stub. Lost wax casting of titanium requires specialized vacuum casting equipment not typically used for noble and base metal alloys, to avoid denegrating the titanium. On the other hand, metal copings made of noble metals such as gold (Au), silver (Ag) and/or palladium (Pd) or base metals such as nickel (Ni) or beryllium (Be) can cause allergic reactions. After casting, the cast metal coping is hand finished to a thickness as small as 0.2 millimeters (mm). Such hand working is difficult and can result in holes in the coping that require the coping to be recast.

Prior to applying porcelain to the coping, the mandrel is removed. Titanium copings usually have a covering of opaque porcelain baked on the coping to hide the $TiO/TiO_2$ film. The baked-on porcelain also helps to bond the porcelain veneer to the titanium coping. The translucent porcelain layers are then applied atop the baked porcelain layer and fired. After the porcelain has been fired and machined to finish the crown, the metal and porcelain crown are bonded to the tooth stub.

Recently, instead of forming a crown or coping with the lost wax technique, a computer aided design/computer aided engineering (CAD/CAM) process has been developed to shape copings for porcelain crowns. The machinery for this is fairly expensive, however, and the coloring of the coping can still affect the crown color. Moreover, pressure from the automated tools that shape the coping becomes problematic at a coping thickness of a few tenths of a millimeter.

SUMMARY

A coating for a biomedical device is disclosed, including a metal layer and/or a ceramic layer, such as a layer of titanium (Ti) and a layer of titanium-nitride (TiN). In one embodiment, an apparatus is disclosed including a titanium (Ti) layer including at least ninety atomic percent titanium (Ti); a titanium-nitride (TiN) layer that is attached to the titanium layer, the titanium-nitride (TiN) layer having a thickness that is less than the thickness of the titanium (Ti) layer, the titanium-nitride (TiN) layer including at least forty atomic percent titanium (Ti) and at least forty atomic percent nitrogen (N); and a porcelain layer that is bonded to the titanium-nitride (TiN) layer, the porcelain layer having a thickness that is greater than thickness of the titanium (TiN) layer. The apparatus can be a crown for a tooth.

Methods for making and using a biomedical device are also disclosed, including vapor deposition of metal and/or ceramic layers, such as titanium (Ti) and titanium-nitride (TiN) layers. In one embodiment, the method includes forming a titanium (Ti) vapor that solidifies to form a titanium (Ti) layer; forming a titanium-nitride (TiN) vapor that coats the titanium (Ti) layer with a titanium-nitride (TiN) layer; and forming a porcelain layer on the titanium-nitride (TiN) layer. The porcelain can be fired to form a dental crown or other device.

DETAILED DESCRIPTION

Figure 1:
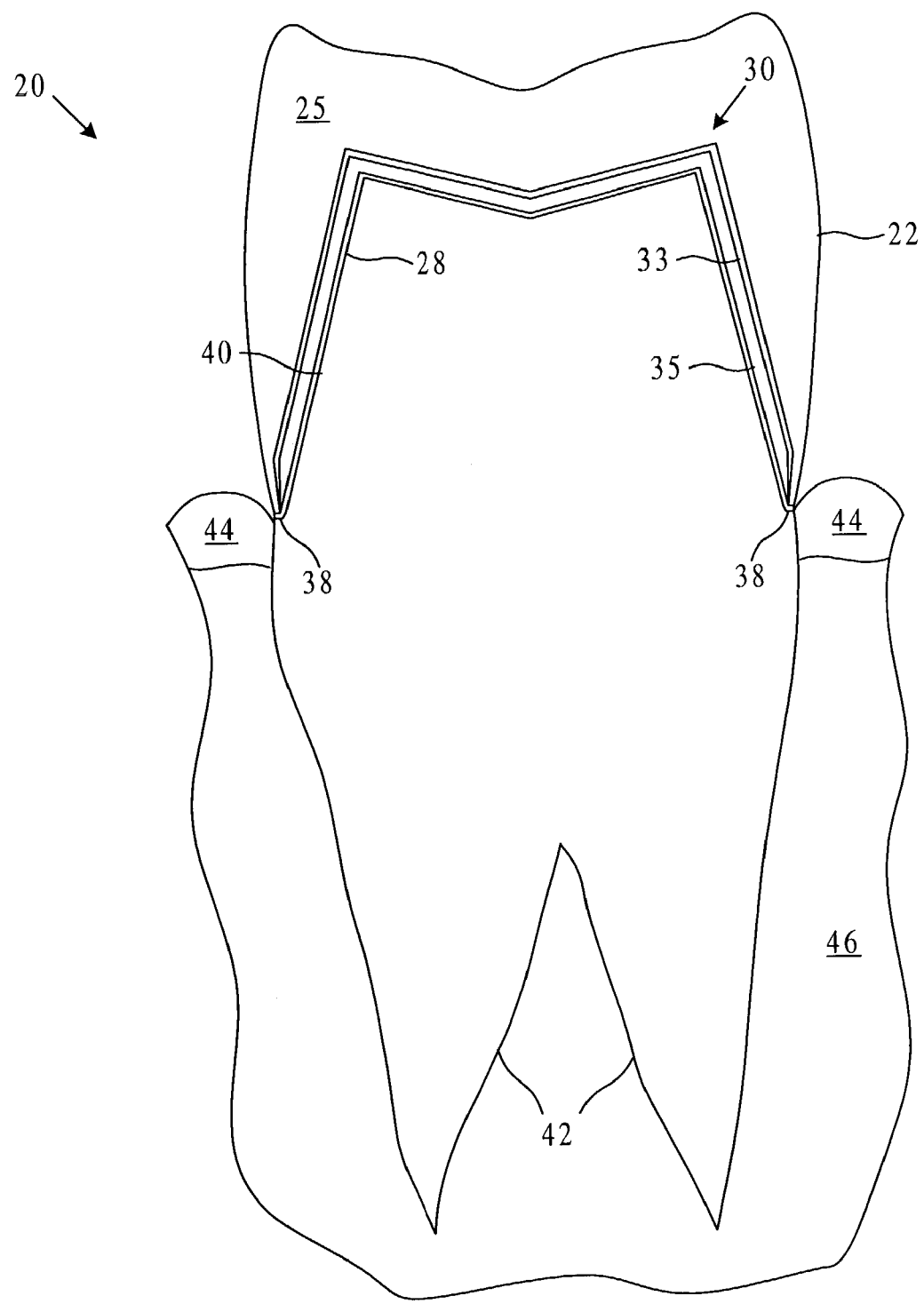
FIG. 1 is a cross-sectional view of a person's tooth, including a prosthetic crown.

A cross-sectional view of a person's tooth 20 is shown in FIG. 1. The tooth 20 has a crown 22 including a porcelain layer 25 that is attached to a metal coping 30. The coping 30 includes a titanium-nitride (TiN) layer 33 disposed on a titanium (Ti) layer 35. In another embodiment, the coping may also include an inner layer of TiN upon which Ti layer 35 is disposed. The coping 30 is bonded with a cement layer 28 to a stub 40 of the tooth 20, the stub having been machined by a dentist to prepare for attachment of the crown 22. The machining was terminated at a lip near a top of the gums 44, the cement bonding the coping and porcelain to the lip in a margin region 38. Also shown are roots 42 of the tooth 20 that extend through a jaw bone 46.

Figure 2:
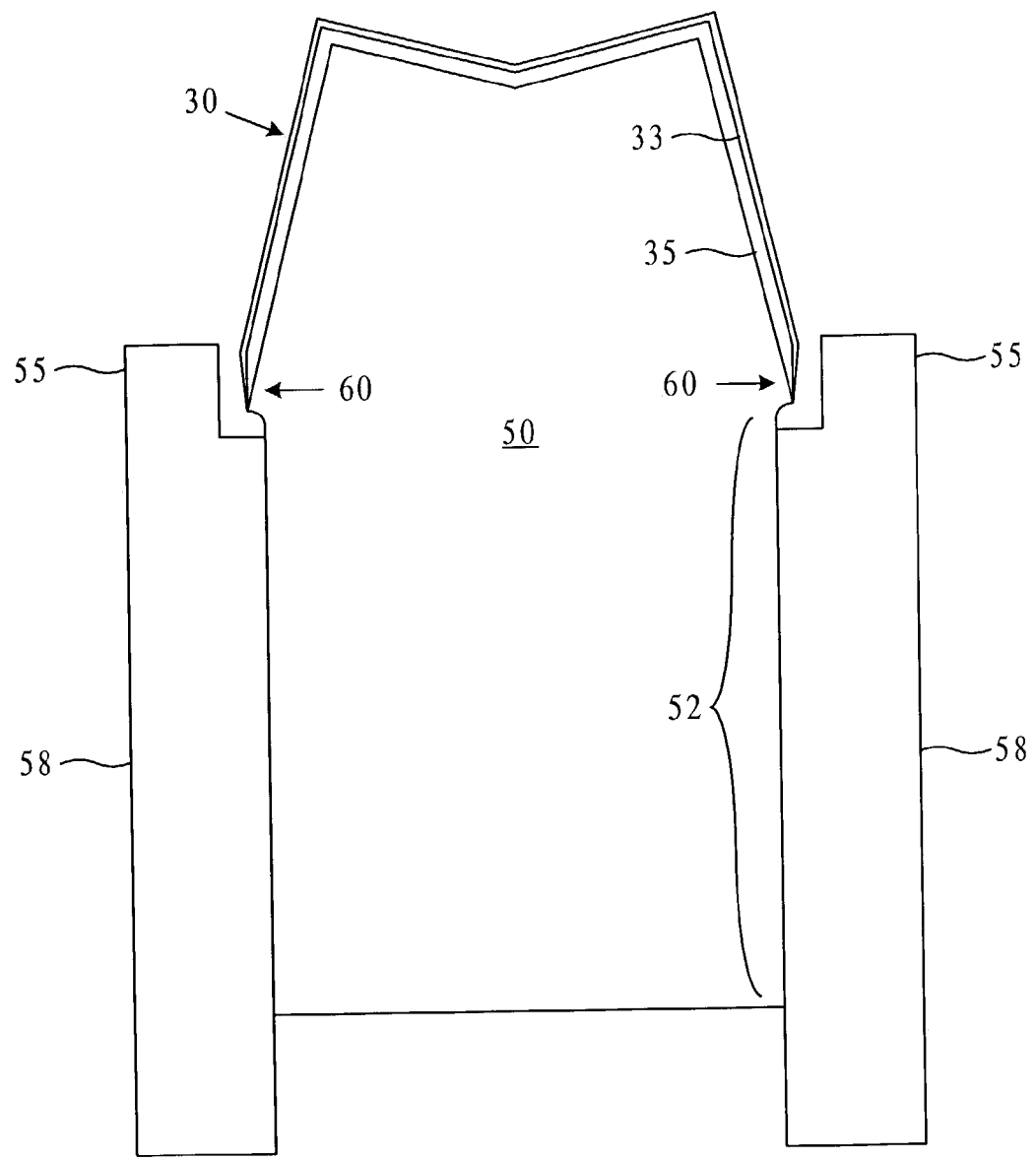
FIG. 2 is a cross-sectional view of a mandrel upon which a coping of the crown was formed.
Figure 4:
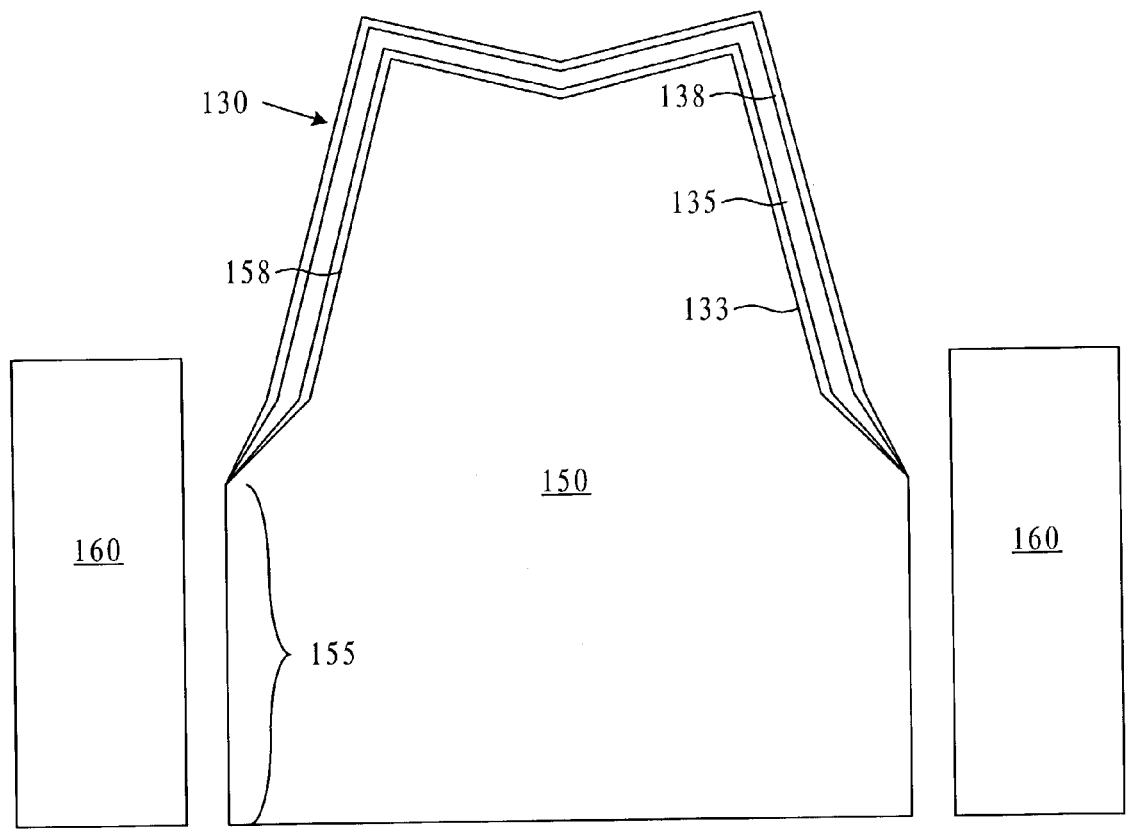
FIG. 4 is a cross-sectional view of a mandrel including a tooth mold upon which a three-layer coping has been formed.

FIG. 2 is a cross-sectional view of a mandrel 50 upon which coping 30 has been formed. The mandrel 50 may for example be a die stone that has been formed from an impression of the tooth stub 40, not shown in this figure. The coping has been formed by physical vapor deposition (PVD), such as cathodic arc deposition, sputtering, ion beam deposition, molecular beam deposition, etc. The mandrel in this embodiment has a handle portion 52 that is slightly recessed compared to the tooth stub portion upon which the coping is formed. In other embodiments the handle portion may not be recessed but may instead be even with or wider than the tooth stub portion. The handle portion is held by clamps 58 which each have a projection 55 that extends adjacent the coping beyond the handle region. The projections 55 provide a shadow during PVD that tapers and terminates ends 60 of the coping 30. Similar projections 160 are shown in FIG. 4.

Figure 3:
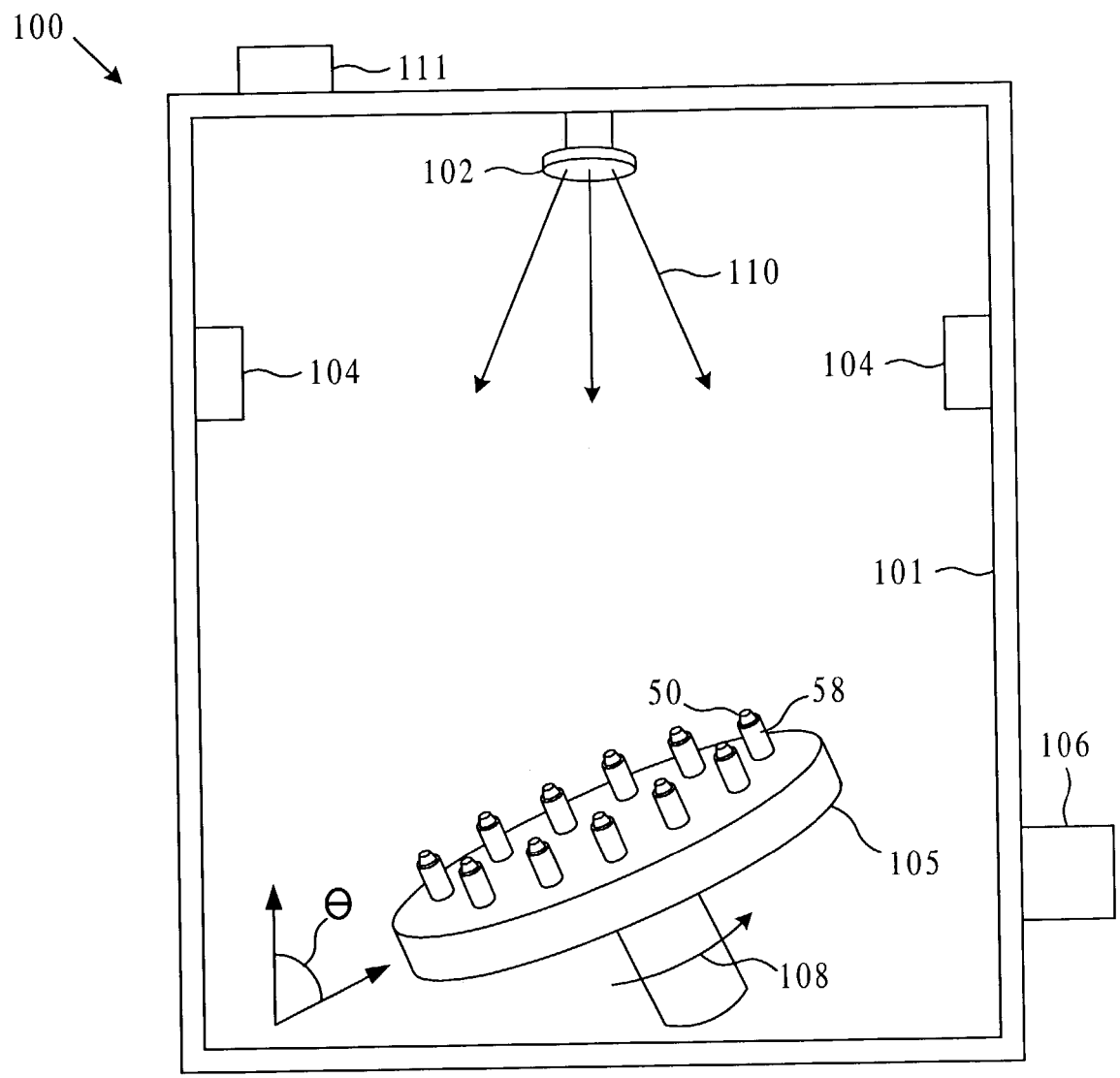
FIG. 3 is a schematic diagram of a physical vapor deposition system in which a coping or other biomedical device may be formed.

FIG. 3 shows a physical vapor deposition system 100 in which a coping or other biomedical device may be formed. The system 100 has a chamber 101 that may be evacuated by vacuum pump 106 to a pressure of $10^{-4}$ Torr or below. Within chamber 101 a moveable platter or pallet 105 holds mandrel 50 as well as a plurality of other mandrels, for receiving material from a target 102 such as a metal cathode. Platter 105 can rotate, as shown by arrow 108, and can tilt to various angles θ from normal to the direction of physical vapor flow from target 102.

Anode or anodes 104 are disposed near cathode 102, which may be made of titanium, zirconium, hafnium or other selected metals. An arc is created between the anode 104 and cathode 102 that generates metal ions as well as some macroparticles at the cathode, the ions and macroparticles traveling generally toward the tilted, rotating platter 105 as shown by arrows 110. Application of a magnetic field and a curved path, not shown in this embodiment, can be used to filter out the macroparticles so that a reduced proportion of macroparticles impinge upon mandrel 50. In another embodiment, system 100 can be a sputtering system or ion beam deposition system. Combination of various physical vapor deposition systems can also be used to deposit various materials on mandrel 50 and the other mandrels on moveable platter 105.

Addition of a gas such as nitrogen via gas inlet 111 can cause formation of a ceramic such as TiN on mandrel 50. In this manner a three-dimensional thin-shelled atomic vapor or molten droplet deposited biomedical prosthetic device can be formed of various metals and ceramics. One embodiment described in this application is a restorative dental crown coping device. Once the coping has been formed on mandrel 50, for example with a layer of Ti and a layer of TiN as shown in FIG. 2, the mandrel can be removed from the coping and porcelain applied to the coping.

Alternatively, mandrel 50 material can be removed after a porcelain layer or layers have been formed on the coping. This can be particularly advantageous for the situation in which a very thin coping 30 is desired, e.g., a coping thickness less than 0.2 mm. In this case, stress from the porcelain as it hardens could alter the coping shape. In the prior art this problem has not been encountered because such a thin coping could not be produced. After the porcelain has been sintered the mandrel material is removed by grinding and optional etching. In this situation it is desirable to use an etchant that does not react with porcelain. It is also possible to use a mandrel material that does not harden when the porcelain is fired.

In contrast with conventional porcelain crowns, the step of applying and firing an initial layer of opaque porcelain is not necessary. This is because the porcelain bonds to the TiN layer and so the baked on layer is not needed for strength. This is also because the TiN layer is a golden color that is close to the color of natural dentin, instead of the black color of titanium oxide or the silver color of other metals, and so the baked-on opaque porcelain layer is not needed for aesthetics. Applying and firing an initial opaque layer of porcelain to the coping 30 is therefore optional. It is also possible to provide an additional bonding layer of porcelain.

The mandrel 50 or die stone can be removed by grinding and/or etching, to yield a coping formed entirely by PVD. While the coping 30 is held with special tweezers translucent porcelain is then applied to the coping in the shape of the tooth. After glazing or firing the porcelain at a high temperature the porcelain finish can be ground and polished to replicate the shape of a natural tooth, yielding the porcelain-on-metal crown 22. The crown can be bonded to the tooth stub 40 with cement 28, restoring the functioning of the tooth 20.

A number of advantages are provided by this dental restoration system. One of the benefits is a reduced cement thickness variation, due to the more accurate fit of the dental crown coping to the die stone or mandrel made by physical vapor deposition compared to the fit of a coping made by the lost wax technique. Another benefit of the replication process is the improved margin region 38 fit between the coping layers and the tooth dentin and enamel, again due to the improved accuracy of PVD compared to lost wax formation. The improved margin fit may be in a range between about 0.1 microns ($\mu$m) and 5.0 $\mu$m. The nominal cement layer 28 thickness may be in a range between about 5 $\mu$m and 50 $\mu$m.

An additional benefit is the ability to precisely control the thickness and properties of plural coping layers. For example, an inner layer that interfaces with the tooth via the cement may be formed of TiO or TiN, a structural layer that provides most of the strength of coping structure may be formed of Ti and an outer layer that bonds with dental porcelain is formed in this embodiment of TiN. The plural layers have material properties and thickness than are independently and precisely controlled with the deposition process and materials selection, as discussed below. The combined thickness of the vapor-deposited layers making up the dental crown coping are typically 0.05 millimeters (mm) to 3.0 mm with a thickness tolerance typically ranging from less than 1 $\mu$m to about 0.05 mm. Due to the reduced and more accurate thickness of both the coping and the cement, the amount of tooth that is removed in preparation for a dental crown restoration is typically reduced by as much as a few millimeters compared to conventional porcelain crowns.

The angle θ at which the physical vapor is deposited with respect to substrate normal ranges between about 5° and 75° full width half maximum (FWHM) A preferred FWHM of deposited vapor is about 45° while platter 105 is rotating to deposit sufficient thickness of metal and/or ceramic layers on all sides of mandrel 50 shown in FIG. 3. Thermal, electron beam and laser beam evaporation or thermal spraying methods, such as flame spraying or plasma arc spraying may be used. Cathodic arc deposition may be a preferred method due to its high deposition rate, which may range between about 0.1 $\mu$m/min and 20 $\mu$m/min, and the large fraction of energetic atomic vapor species to droplet species in the deposition vapor stream between the deposition source and dental mandrel. It has been discovered that a deposited ratio of (atomic vapor)/(molten droplets) greater than about 0.5 results in favorable metal and ceramic layers. This ratio can be significantly higher than 0.5 when the macroparticles are filtered out as described above.

The deposited layers can be single inorganic layers or multiple (e.g., up to 1000) layers. The layers can include inorganic metals, nitrides, carbides and oxides. Typical metals used for PVD of the layers include titanium, zirconium, molybdenum, tungsten, tantalum, niobium vanadium chromium, nickel, iron, copper, beryllium, ruthenium, rhodium, platinum, palladium, hafnium, silicon, aluminum, gold, silver and their alloys. Nitrides and carbides of titanium, zirconium, molybdenum, tungsten, tantalum, vanadium, niobium, aluminum and hafnium can be formed for the coping or other biomedical layers. Oxides of titanium, zirconium, molybdenum, tungsten, tantalum, niobium vanadium chromium, nickel, iron, copper, ruthenium, rhodium, platinum, hafnium, silicon and aluminum may also be used.

Typical deposited layer thickness for biomedical embodiments range from 10 Å to 5 mm depending on the intended application. Titanium and its nitrides, oxides and carbides can be advantageous because of the known biocompatibility of these materials with mammals. Instead of a coating a substrate that is removed, a coating can be formed on a device that is not removed, such as a Ti wire coated with TiN. Alternative organic materials, such as polyimide, polyester and teflon can be used as single layers or combined with inorganic materials as described previously. Typically organic layer thickness range from 1000 Å to 5 mm in thickness.

FIG. 4 is a cross-sectional view of a substrate mandrel 150 upon which a three-layer coping 130 has been formed. As described above, the mandrel 150 may for example be a die stone that has been formed from an impression of the tooth stub, not shown in this figure. The mandrel 150 may consist of common dental ceramic or polymer mold materials that are vacuum compatible. Various methods of forming a die stone replicating the desired tooth shape are known and used by dental laboratories. Other mandrel fabrication methods and materials consisting of metals such as aluminum, copper, stainless steel, epoxy, polyamide or other polymer materials can be used.

The coping 130 has been formed by physical vapor deposition, such as cathodic arc deposition, sputtering, ion beam deposition, molecular beam deposition, etc. An inner layer 133 of the coping is formed of TiN, a middle layer 135 of the coping is formed of Ti, and an outer layer of the coping is formed of TiN in this embodiment. Other metals and their ceramic oxides, nitrides or oxynitrides may be employed in other embodiments. The middle layer 135 is typically thicker than both the inner layer 133 and the outer layer 138. A porcelain layer 140 has been formed on and bonded to the coping to form a crown 144. The mandrel 150 in this embodiment has a handle portion 155 that is substantially flush with the largest portion of the positive mold 158 of the tooth stub, upon which the coping 130 is formed. The tooth stub mold 158 has tapered sides and a tapered flange at a base that meets the handle 150. The coping layers 133, 135 and 138 each have a tapered thickness adjacent to the base, which may be created by a shadow during PVD. The tapered portion of layers 133, 135 and 138 extend about 0.05 mm to 2.0 mm.

The inner layer 133 of TiN may have a thickness ranging between about 1000 Å and 50 μm, the middle layer 135 of Ti metal may have a thickness ranging between about 0.005 mm and 10 mm, and the outer layer 138 of TiN may have a thickness ranging between about 1000 Å and 50 μm. The inner layer 133 provides the bonding interface between the coping layers 130 and the cementing layer bonding the coping to the tooth. The inner layer 133 may include vapor-deposited titanium-nitride, oxynitride or zirconium-nitride, oxide or oxy-nitride. These materials exhibit a yellow gold like optical reflective quality that may be preferred under a translucent cement layer and tooth dentin and enamel. Titanium oxide, which is black, may instead form the inner layer 133. The outer layer 138 may include vapor-deposited titanium-nitride, titanium oxynitride, zirconium nitride, zirconium or zirconium oxy-nitride. These materials exhibit a yellow gold like optical reflective quality that may be preferred under a translucent cement layer and tooth dentin and enamel. Zirconium oxide, which is white, may instead form the outer layer 138.

The mandrel 150 material can be removed from the deposited layers which form the dental coping 130. Typical dental ceramic mandrel material may be removed with a small hand grinder and then grit blasted or chemical etched in a basic pH solution to remove the remaining mandrel residual material. Such hand grinder and grit blasting techniques are known in the dental laboratories. The basic solution consists of a KOH or NaOH solution with a PH ranging from 8–14. High-pressure steam cleaning or steamer and water in an ultrasonic bath are a method of removing the residual mandrel material.

Figure 5:
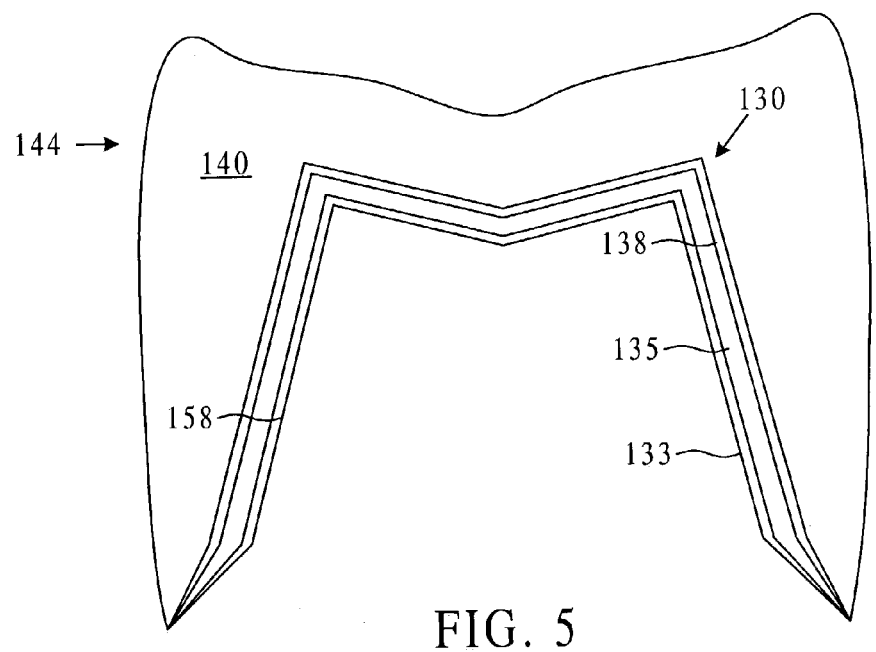
FIG. 5 is a cross-sectional view of a crown for a tooth, the crown including a porcelain layer bonded to the coping of FIG. 4.

Typical dental porcelain layers can then be applied and sintered onto the outer layer 138, yielding a porcelain fused to metal (PFM) crown shown in FIG. 5. The dental porcelain materials and firing or baking process can be those known and used in dental laboratories. Instead of porcelain layer 140, such a crown can be made from all metal and/or ceramic layers that have been formed by physical vapor deposition. For example, such a crown could be made of the coping layers 133, 135 and 138 described above, followed by a layer of ceramic such as zirconium-nitride (ZrN), which is white in color and can be polished as desired. Porcelain or ceramic tooth veneers can be similarly formed.

Alternatively, the mandrel 150 material such as gypsum can be removed after the porcelain layer 138 or layers have been formed on the coping. This can be particularly advantageous for the situation in which a very thin coping 130 is desired, e.g., a coping thickness less than 0.2 mm. In this case, stress from the porcelain as it hardens could alter the coping shape. In the prior art this problem has not been encountered because such a thin coping could not be produced. After the porcelain has been sintered the mandrel material is removed by grinding and optional etching. In this situation it is desirable to use an etchant, such as $HNO_3$ HCL $H_2SO_4$ NaOH or KOH, that does not react with porcelain.

Figure 6:
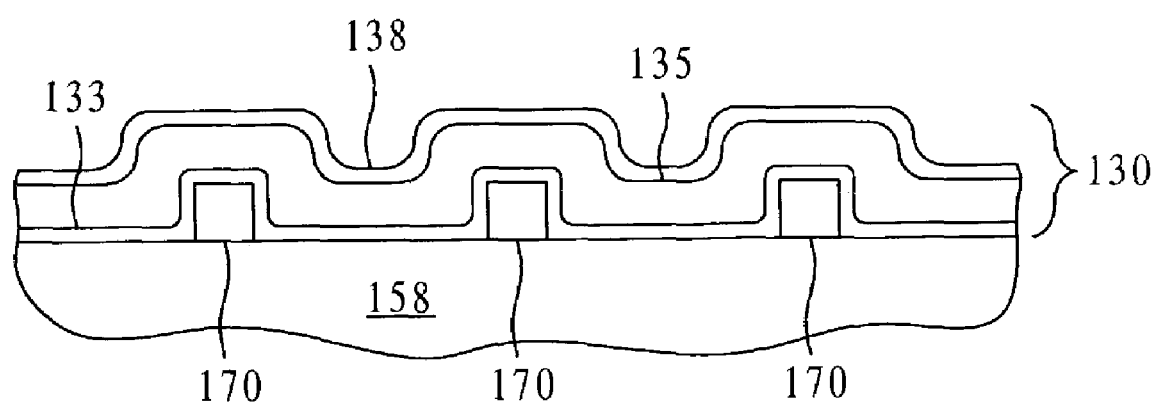
FIG. 6 is a cross-sectional view of a portion of the tooth mold of FIG. 4 with a plurality of attached protrusions that affect the texture of the coping.

FIG. 6 is a cross-sectional view of a portion of the tooth mold 158 with a plurality of attached protrusions 170 that affect the texture of the coping 130. The protrusions 170 in this embodiment have a generally rectangular cross-sectional shape, but other protrusions having cross-sectional shapes such as circular, oblong, oval, triangular, or irregular may instead be employed. The coping layers 133, 135 and 138 replicate the mandrel mold 158 with the residing protrusions 170. The protrusions 170 have widths and heights that typically range between obout 0.5 μm and 1.0 mm. The substrate mandrel is removed leaving the dental coping shell 130 with pockets that replicate the protrusions. The substrate mandrel and formed substrate protrusions, which may be made of the same or different materials, may be removed from the shell 130 by the same method as described earlier.

Further details of an embodiment like that shown in FIG. 1 are described below. In one aspect the device is a titanium/titanium-nitride based alloy intended for use as a base metal alloy in the making of single unit device porcelain-fused-to-metal (PFM) prosthetic dental materials and custom-made dental prosthetic devices, such as a porcelain-to-metal veneer for a tooth. Such a device can be a single unit coping device, i.e., a PFM dental restorative device that may be used for all anterior and posterior tooth dental crown restorations.

The device may be manufactured by a dental laboratory to the prescribed dimensions and fit instructed by a dentist, in accordance with an impression made by the dentist. The device can be formed of unalloyed Ti metal (Grade 2) deposited by cathodic arc deposition onto a suitable dental stone positive mold replica of the desired tooth shape, from the impression, to be fitted with a dental coping substructure. The cathodic arc deposition includes a Ti cathode material, metal plasma in vacuum, sustained by a guided plasma arc on the cathode surface. The mold is rotated at a predetermined angle in a vacuum environment while Ti metal is deposited onto the mold. The deposited Ti material forming the dental coping structure is accomplished by transporting the Ti metal vapor from the Ti plasma originating from the unalloyed Ti cathode to the rotating ceramic mold. The deposited Ti metal thickness forming the dental coping wall thickness is controlled by the total deposition time $Ti_{(dep)}$ (min.) calculated from the known deposition rate $Ti_{(rate)}$ ($\mu$m/min.) of the Cathodic Arc Source and the targeted wall thickness $Ti_{(wall)}$ ($\mu$m) of the titanium dental coping. That is, $$Ti_{(dep)}(\text{min.}) = [Ti_{(wall)} (\mu m)]/[Ti_{(rate)} (\mu m/\text{min.})].$$

Typical Ti wall thickness ranges from 100 $\mu$m–350 $\mu$m. The dental coping wall thickness can made to the thickness desired by the dental laboratory. The second layer forming the exterior of the dental coping consists of TiN, deposited directly after the Ti layer without interrupting the deposition process or vacuum environment. The TiN layer is formed by the addition of high purity nitrogen gas (99.99% purity), into the Ti metal plasma under vacuum. The nitrogen gas reacts with the Ti plasma and forms the TiN chemical compound on the Ti surface. The overall atomic concentration of Ti in the TiN layer may range between about 45% and 55%, and the overall atomic concentration of N in the TiN layer may also range between about 45% and 55%. The TiN layer forms the exterior surface of the dental coping and bonds to the porcelain veneer material. Typical TiN thickness is in a range between about 10 $\mu$m and 20 $\mu$m.

After the Ti metal and TiN layers are deposited, the mold material can be removed by using tools typically used by dental laboratories. The bulk of the mold material can be removed by hand grinding, followed by abrasive alumina grit blasting. The final Ti/TiN dental coping fit can be adjusted by hand grinding until the proper fit to master mold is obtained. The dental porcelain can be applied to the exterior TiN layer by the dental laboratory. Vita Titanium Porcelain, available from Vident Corporation, 3150 East Birch Street, Brea, Calif. 92821, is one type of porcelain that has been used with success. A dentist can fit and cement the finished PFM crown onto the prepared tooth.

Table 1 on the following page list some specifications of this embodiment, in which LSL refers to a lower specification limit, and USL refers to an upper specification limit.

TABLE 1

| DESCRIPTION | NOMINAL | TOLERANCE |
|---|---|---|
| Titanium Cathode Composition. | Titanium Grade 2 | Titanium Grade 2 |
| Deposited Titanium Dental coping composition. | Titanium Grade 2 | Titanium Grade 2 |

TABLE 1-continued

| DESCRIPTION | NOMINAL | TOLERANCE |
|---|---|---|
| Deposited Titanium-nitride Composition. | $Ti_{.50}N_{.50}$ (atomic concentration) | USL = $Ti_{.45}N_{.55}$ USL = $Ti_{.55}N_{.45}$ |
| Dental coping wall thickness Titanium metal 100 $\mu$m–350 $\mu$m. | As specified by Dental Laboratory, end-user. | USL = +10% OF AVG. LSL = −10% OF AVG. |
| Dental coping wall thickness Titanium-nitride. | 10 $\mu$m | LSL = 5 $\mu$m USL = 20 $\mu$m |
| Density | 4.74 gm/cm$^3$ | LSL = 4.24 gm/cm$^3$ USL = 5.24 gm/cm$^3$ |
| Proof Stress | 265 Mpa | LSL = 250 MPa USL = 300 MPa |
| Modulus | 61 GPa | LSL = 50 GPa USL = 100 GPa |
| Elongation | 8.5% | LSL = 3% USL = 20% |
| Coeff. Of Exp. 25–500° C. | 8.8 × 10$^{-6}$K$^{-1}$ | LSL = 8.3 × 10$^{-6}$K$^{-1}$ USL = 9.3 × 10$^{-6}$K$^{-1}$ |
| Porcelain Bond | 35 Mpa | LSL > 25 MPa USL = 100 MPa |

Table 2 provides a chemical analysis of some Ti sample layers that were cathodic arc deposited on a silicon wafer.

TABLE 2

| ELEMENT | Ti Coping Layer Maximum Values Wt. % |
|---|---|
| Nitrogen, max. | .006 |
| Carbon, max | .013 |
| Hydrogen, max | .0012 |
| Iron, max | .06 |
| Oxygen, max. | .069 |
| Aluminum | .01 |
| Vanadium | .0033 |
| Tin | .0042 |
| Ruthenium | <.00001 |
| Palladium | <.00005 |
| Cobalt | .00016 |
| Molybdenum | .0013 |
| Chromium | .0130 |
| Nickel | .0058 |
| Niobium | .00044 |
| Zirconium | .0015 |
| Silicon | .0015 |
| Residuals, max. each | .06 |
| Residuals, max., total | .145 |
| Titanium, balance | 99.77 |

Table 3 provides a chemical analysis of some 10 $\mu$m–20 $\mu$m thick TiN sample layers that were cathodic arc deposited on 100 $\mu$m–200 $\mu$m thick Ti layers.

TABLE 3

| SAMPLE | Ti (at. %) | N (at. %) |
|---|---|---|
| 1 | 52.0 | 48.0 |
| 2 | 53.0 | 47.0 |
| MEAN | 52.5 | 47.5 |

The mean composition of two TiN samples consist of titanium 52.5% and nitrogen 47.5% (atomic percent), +/−5% uncertainty, as measured by Rutherford Backscatter Analysis. Stoichiometric TiN is Titanium 50% and Nitrogen 50. The measured TiN composition of the Nano-TiCrown™ is equivalent to stoichiometric TiN compound. The Ti/TiN porcelain fused to metal crowns have also been successfully tested for metal-ceramic bond strength requirements, thermal expansion coefficient (CTE) requirements, and biocompatibility requirements.

Although the above description has focused on illustrating exemplary PVD biomedical devices and methods, other devices and methods can be formed in accordance with the teachings of this disclosure. Moreover, other embodiments and modifications of this disclosure will be apparent to persons of ordinary skill in the art in view of these teachings. Therefore, the methods and devices taught in this invention are not limited, and can be applied to other biomedical devices, electronic and optical devices.

What is claimed is:

1. An apparatus comprising:
   a titanium (Ti) layer including at least ninety atomic percent titanium (Ti);
   a titanium-nitride (TiN) layer that is attached to the titanium layer, the titanium-nitride (TiN) layer having a thickness that is less than that of the titanium (Ti) layer, the titanium-nitride (TiN) layer including at least forty atomic percent titanium (Ti) and at least forty atomic percent nitrogen (N); and
   a porcelain layer that is bonded to the titanium-nitride (TiN) layer, the porcelain layer having a thickness that is greater than thickness of the titanium (TiN) layer.

2. The apparatus of claim 1, wherein the porcelain layer has an outer surface with a shape that substantially matches that of a tooth.

3. The apparatus of claim 1, wherein the porcelain layer is part of a crown for a tooth.

4. The apparatus of claim 1, wherein the porcelain layer is part of a veneer for a tooth.

5. The apparatus of claim 1, wherein the titanium (Ti) layer has a substantially concave surface and a substantially convex surface, and the titanium-nitride (TiN) layer is attached to the substantially convex surface.

6. The apparatus of claim 1, wherein the titanium-nitride (TiN) layer has a thickness that is less than one-half millimeter, and the titanium (Ti) layer has a thickness that is less than three millimeters.

7. The apparatus of claim 1, wherein the titanium (Ti) layer has a plurality of pockets disposed on a surface that is distal to the titanium-nitride (TiN) layer.

8. The apparatus of claim 1, wherein the titanium (Ti) layer has a tapered end.

9. The apparatus of claim 1, wherein the titanium (Ti) layer is formed by cathodic arc deposition.

10. The apparatus of claim 1, wherein titanium (Ti) layer and the titanium-nitride (TiN) layer have a combined thickness that is less than 0.2 millimeters.

11. A method comprising:
    forming a titanium (Ti) vapor that solidifies to form a titanium (Ti) layer;
    forming a titanium-nitride (TiN) vapor that coats the titanium (Ti) layer with a titanium-nitride (TN) layer; and
    forming a porcelain layer on the titanium-nitride (TiN) layer.

12. The method of claim 11, further comprising providing a mold of a tooth, over which the titanium (Ti) layer is formed.

13. The method of claim 11, further comprising forming a titanium-nitride (TiN) underlayer, on which the titanium (Ti) layer is formed.

14. The method of claim 11, further comprising forming a titanium-oxide (TiO) underlayer, on which the titanium (Ti) layer is formed.

15. The method of claim 11, further comprising positioning a device adjacent to the titanium (Ti) layer to partially block the titanium (Ti) vapor.

16. The method of claim 11, wherein forming a titanium (Ti) vapor includes ionizing a titanium (Ti) target.

17. The method of claim 11, further comprising forming titanium (Ti) macroparticles along with the titanium (Ti) vapor, wherein the titanium (Ti) layer has a greater volume formed from the titanium (Ti) vapor than from the titanium (Ti) macroparticles.

18. The method of claim 11, further comprising:
    forming a mandrel over which the titanium (Ti) layer is formed; and removing the mandrel after the porcelain layer has been formed on the titanium-nitride (TiN) layer.

19. The method of claim 11, wherein the titanium (Ti) layer, the titanium-nitride (TiN) layer and the porcelain layer form a dental device, and further comprising attaching the dental device to a tooth portion.

20. A biomedical device comprising:
    a layer of titanium (Ti) having a thickness that is less than two millimeters, the titanium (Ti) layer having a concave surface and a convex surface;
    a layer of titanium-nitride that is bonded to the convex surface of the titanium (Ti) layer, the titanium-nitride (Ti) layer having a thickness that is less than the thickness of the titanium (Ti) layer; and
    a porcelain layer that is bonded to the titanium-nitride (TiN) layer;
    wherein the device fits within a mammal and is biocompatible with the mammal.

21. A biomedical device comprising:
    a layer of titanium (Ti) having a thickness that is less than two millimeters, the titanium (Ti) layer having a concave surface and a convex surface;
    a layer of titanium-nitride (TiN) that is bonded to the convex surface of the titanium (Ti) layer, the titanium-nitride (TiN) layer having a thickness that is less than the thickness of the titanium (Ti) layer; and
    a porcelain layer that is bonded to the titanium-nitride (TiN) layer:
    wherein the device fits within a mammal and is biocompatible with the mammal and the porcelain layer has an outer surface shaped to match that of a tooth.

22. A biomedical device comprising:
    a layer of titanium (Ti) having a thickness that is less than two millimeters, the titanium (Ti) layer having a concave surface and a convex surface;
    a layer of titanium-nitride (TiN) that is bonded to the convex surface of the titanium (Ti) layer, the titanium-nitride (TiN) layer having a thickness that is less than to thickness of the titanium (Ti) layer; and
    a second titanium-nitride (TiN) layer that is bonded to the concave surface of the titanium (Ti) layer;

wherein the device fits within a mammal and is biocompatible with the mammal.

23. A biomedical device comprising:

a layer of titanium (Ti) having a thickness that is less than two millimeters, the titanium (Ti) layer having a concave surface and a convex surface;

a layer of titanium-nitride (TiN) that is bonded to the convex surface of the titanium (Ti) layer, the titanium-nitride (TiN) layer having a thickness that is less than the thickness of the titanium (Ti) layer; and a titanium-oxide (TiO) layer that is bonded to the concave surface of the titanium (Ti) layer;

wherein the device fits within a mammal and is biocompatible with the mammal.

* * * * *

UNITED STATES PATENT AND TRADEMARK OFFICE
CERTIFICATE OF CORRECTION

PATENT NO.         : 6,994,550 B2
APPLICATION NO. : 10/622626
DATED                 : February 7, 2006
INVENTOR(S)       : Knapp et al.

It is certified that error appears in the above-identified patent and that said Letters Patent is hereby corrected as shown below:

In column 9, line 33, add the following word in claim 1:

--the-- should be added after "than" and before "thickness" to read --than the thickness--

In column 9, line 33, correct the following word in claim 11:

"titanium" should be --titanium-nitrade--

In column 9, line 64, correct the following word in claim 11:

"(TN )" should be --(TiN)--

In column 10, line 35, add the following word in claim 20:

--(TiN)-- should be added after "titanium-nitrade" and before "that" to read --titanium-nitrde (TiN) that--

In column 10, line 37, correct the following word in claim 20:

"(TN)" should be --(TiN)--

UNITED STATES PATENT AND TRADEMARK OFFICE
CERTIFICATE OF CORRECTION

PATENT NO.       : 6,994,550 B2
APPLICATION NO.  : 10/622626
DATED            : February 7, 2006
INVENTOR(S)      : Knapp et al.

It is certified that error appears in the above-identified patent and that said Letters Patent is hereby corrected as shown below:

In column 10, line 53, correct the following punctuation in claim 21:

":" should be --;--

In column 10, line 64, correct the following word in claim 22:

"to" should be --the--

Signed and Sealed this

Twenty-sixth Day of September, 2006

JON W. DUDAS
*Director of the United States Patent and Trademark Office*